(12) United States Patent
Zhang

(10) Patent No.: US 11,318,252 B2
(45) Date of Patent: May 3, 2022

(54) LOW FORCE TRIGGER

(71) Applicant: OWEN MUMFORD LTD, Oxfordshire (GB)

(72) Inventor: Kuiwei Zhang, Oxfordshire (GB)

(73) Assignee: OWEN MUMFORD LTD, Oxfordshire (GB)

( * ) Notice: Subject to any disclaimer, the term of this patent is extended or adjusted under 35 U.S.C. 154(b) by 213 days.

(21) Appl. No.: 16/494,339

(22) PCT Filed: Mar. 15, 2018

(86) PCT No.: PCT/GB2018/050660
§ 371 (c)(1),
(2) Date: Sep. 16, 2019

(87) PCT Pub. No.: WO2018/167491
PCT Pub. Date: Sep. 20, 2018

(65) Prior Publication Data
US 2020/0297929 A1  Sep. 24, 2020

(30) Foreign Application Priority Data

Mar. 15, 2017 (GB) ...................................... 1704143

(51) Int. Cl.
*A61M 5/20* (2006.01)
*A61M 5/31* (2006.01)
*A61M 5/32* (2006.01)

(52) U.S. Cl.
CPC ........ *A61M 5/2033* (2013.01); *A61M 5/3146* (2013.01); *A61M 5/3204* (2013.01);
(Continued)

(58) Field of Classification Search
CPC .............. A61M 5/2033; A61M 5/3146; A61M 2005/2073; A61M 2005/2026; A61M 5/20; A61M 2005/2006; A61M 2005/202
See application file for complete search history.

(56) References Cited

U.S. PATENT DOCUMENTS

| 5,540,664 A | 7/1996 | Wyrick |
| 2010/0049125 A1* | 2/2010 | James ................ A61M 5/2033 604/110 |

(Continued)

FOREIGN PATENT DOCUMENTS

| CN | 101641125 A | 2/2010 |
| CN | 103476442 A | 12/2013 |

(Continued)

OTHER PUBLICATIONS

International Preliminary Report on Patentability, dated Sep. 17, 2019, from corresponding PCT application No. PCT/GB2018/050660.

(Continued)

*Primary Examiner* — Bhisma Mehta
*Assistant Examiner* — Neeraja Gollamudi
(74) *Attorney, Agent, or Firm* — Quarles & Brady LLP

(57) ABSTRACT

An injection device for receiving a syringe therein and for delivering a dose of medicament from the syringe, the injection device including: a driver mechanism retainable in a primed state and releasable from the primed state for driving one or more features of the injection device forwards, a trigger mechanism including a ramped surface engaged with the driver mechanism to retain the driver mechanism in the primed state, the trigger mechanism being configured on actuation thereof to withdraw the ramped surface from engagement with the driver mechanism for release thereof.

21 Claims, 9 Drawing Sheets

(52) U.S. Cl.
CPC .............. *A61M 2005/206* (2013.01); *A61M 2005/2073* (2013.01); *A61M 2005/2086* (2013.01)

(56) References Cited

U.S. PATENT DOCUMENTS

| | | | |
|---|---|---|---|
| 2010/0262083 A1* | 10/2010 | Grunhut | A61M 5/2033 604/198 |
| 2013/0324925 A1 | 12/2013 | Brereton et al. | |
| 2016/0008540 A1 | 1/2016 | Fourt et al. | |

FOREIGN PATENT DOCUMENTS

| | | |
|---|---|---|
| CN | 104902945 A | 9/2015 |
| CN | 105025957 A | 11/2015 |
| CN | 105492042 A | 4/2016 |
| GB | 2538566 A | 11/2016 |
| WO | 2008/112472 A2 | 9/2008 |
| WO | 2014/159018 A1 | 10/2014 |
| WO | 2015/011488 A1 | 1/2015 |
| WO | 2016/174245 A1 | 11/2016 |

OTHER PUBLICATIONS

Combined Search and Examination Report issued in UK Patent Application No. GB1704143.5 dated Aug. 14, 2017.
First Office Action from corresponding Chinese Patent Application No. 201880032612.5 dated Apr. 30, 2021 (17 pages) (English translation included).
International Search Report, dated Jul. 3, 2018, from corresponding PCT application No. PCT/GB2018/050660.
Written Opinion, dated Jul. 3, 2018, from corresponding PCT application No. PCT/GB2018/050660.

* cited by examiner

LOW FORCE TRIGGER

CROSS-REFERENCE TO RELATED APPLICATIONS

The present application represents the United States National Stage of International Application No. PCT/GB2018/050660, filed Mar. 15, 2018, which claims priority to British Patent Application Serial No. GB 1704143.5, filed Mar. 15, 2017, and entitled, "LOW FORCE TRIGGER," the contents of which are incorporated herein by reference in their entirety.

TECHNICAL FIELD

This invention relates to injection devices for delivering a dose of medicament from a syringe. In particular, but not exclusively, the invention relates to an autoinjector type device which facilitates powered or power assisted needle insertion and injection.

BACKGROUND

Injection devices are used for the convenient administration of medicaments. For example, injection devices (which may typically be in the form of a pen injector) may be used for providing a single metered dose of a medicament, for example such as Epinephrine in an emergency or for providing regular metered doses of a medicament such as Insulin. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an "autoinjector" device, in which, in addition to automating the delivery of the medicament, the device is also arranged to automate the insertion of a needle into the skin prior to the delivery of the medicament.

Injection devices generally comprise a delivery arrangement which is arranged to automatically deliver a dose from the syringe, and optionally (in the case of an autoinjector) to first displace the syringe within the housing to cause needle penetration. The delivery arrangement generally acts via a plunger which includes or engages a piston (also referred to as a "bung") which is slidably provided within the syringe. In the case of an autoinjector the initial static friction or "stiction" between the bung and syringe resists forward movement of the piston relative to the syringe such that initially the delivery arrangement moves the syringe and piston forward into the needle insertion position. Here, further movement of the syringe is blocked and the delivery arrangement will continue to move forward, overcoming the stiction, and moving the piston and the bung through the syringe.

A common form of delivery arrangement includes a driver mechanism which biases the plunger forwardly and a trigger mechanism which holds the plunger (directly or indirectly) against the force of the driver mechanism until the trigger is released. For example the driver mechanism may comprise a drive spring (for example a compression spring) which is held in an energised (or primed position) prior to release by the trigger.

An injection device of the autoinjector type is described in WO2016/189286.

At least some embodiments of the invention seek to provide an improved injection device which may help to address some of these problems.

SUMMARY

According to an aspect of the invention there is provided an injection device for receiving a syringe therein and for delivering a dose of medicament from the syringe, the injection device comprising: a driver mechanism retainable in a primed state and releasable from the primed state for driving one or more features of the injection device forwards, a trigger mechanism comprising a ramped surface engaged with the driver mechanism to retain the driver mechanism in the primed state, the trigger mechanism being configured on actuation thereof to withdraw the ramped surface from engagement with the driver mechanism for release thereof.

Optionally, the trigger mechanism comprises a rotatable collar, which comprises the ramped surface, and wherein actuation of the trigger mechanism comprises rotation of the collar.

Optionally, the trigger mechanism is configured to translate a linear actuation force into rotation of the collar.

Optionally, the trigger mechanism comprises a trigger lug configured to engage with a ramped section of a trigger track on the collar for rotating the collar.

Optionally, the trigger track further comprises an axial section, and wherein the trigger lug is configured to engage with the axial section, such that rotation of the collar is prevented when the driver mechanism is retained in the primed state.

Optionally, the injection device according to any preceding claim, further comprising a trigger configured to be operated by a user and to actuate the trigger mechanism when operated.

Optionally, the trigger comprises an actuator configured to move rearwards under a force resulting from pressing a forward end of the injection device against an injection site.

Optionally, the trigger comprises a trigger button configured to be operated by depression thereof by the user.

Optionally, the trigger lug is directly coupled to the trigger button or actuator, and wherein operation of the trigger button or actuator causes the trigger lug to engage with the ramped section of the trigger track.

Optionally, the driver mechanism comprises a release lug configured to engage the ramped surface.

Optionally, the driver mechanism exerts a force biasing the release lug onto the ramped surface for assisting withdrawal of the ramped surface.

Optionally, the driver mechanism comprises a compression spring.

Optionally, the driver mechanism is configured to drive forwards one or more of: the syringe for insertion of a needle of the syringe into an injection site; and a plunger of the syringe for delivery of the dose of medicament.

According to the invention in an aspect, there is provided a trigger mechanism for use in an injection device for receiving a syringe therein and for delivering a dose of medicament from the syringe, the trigger mechanism comprising: a ramped surface configured to engage with a driver mechanism to retain the driver mechanism in a primed state, the trigger mechanism being configured such that, on actuation thereof, the ramped surface is withdrawn from engagement with the driver mechanism for release of the driver mechanism.

Optionally, the trigger mechanism further comprises a rotatable collar, which comprises the ramped surface, and wherein actuation of the trigger mechanism comprises rotation of the collar.

Optionally, the trigger mechanism is configured to translate a linear actuation force into rotation of the collar.

Optionally, the trigger mechanism comprises a trigger lug configured to engage with a ramped section of a trigger track on the collar for rotating the collar.

Optionally, the trigger track further comprises a axial section, and wherein the trigger lug is configured to engage with the axial section, such that rotation of the collar is prevented when the driver mechanism is retained in the primed state.

Optionally, the trigger mechanism further comprises a trigger configured to be operated by a user and to actuate the trigger mechanism when operated.

Optionally, the trigger comprises an actuator configured to move rearwards under a force resulting from pressing a forward end of the injection device against an injection site.

Optionally, the trigger comprises a trigger button configured to be operated by depression thereof by the user.

Optionally, the trigger lug is directly coupled to the trigger button or actuator, and operation of the trigger button or the actuator causes the trigger lug to engage with the ramped section of the trigger track.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use. Further, the terms up, down and vertical refer to the situation in which an injection device is held so that the forward end is lowermost and the injection device itself is held vertically. Axial, radial and circumferential are used herein to conveniently refer to the general directions relative to the longitudinal direction of the injection device (or components thereof).

The skilled person will, however, appreciate that these terms are not intended to be narrowly interpreted (and for example, the injection device may have a non-circular and/or irregular form). Typically, regardless of the chosen injection device external profile the syringe or cartridge will have a conventional, generally cylindrical, elongate form and will include or be associated with a needle extending longitudinally from a forward end thereof. Thus, the longitudinal axis of the injection device will typically substantially coincide with (or be parallel to) the axial direction of the syringe or cartridge.

Figure 1:
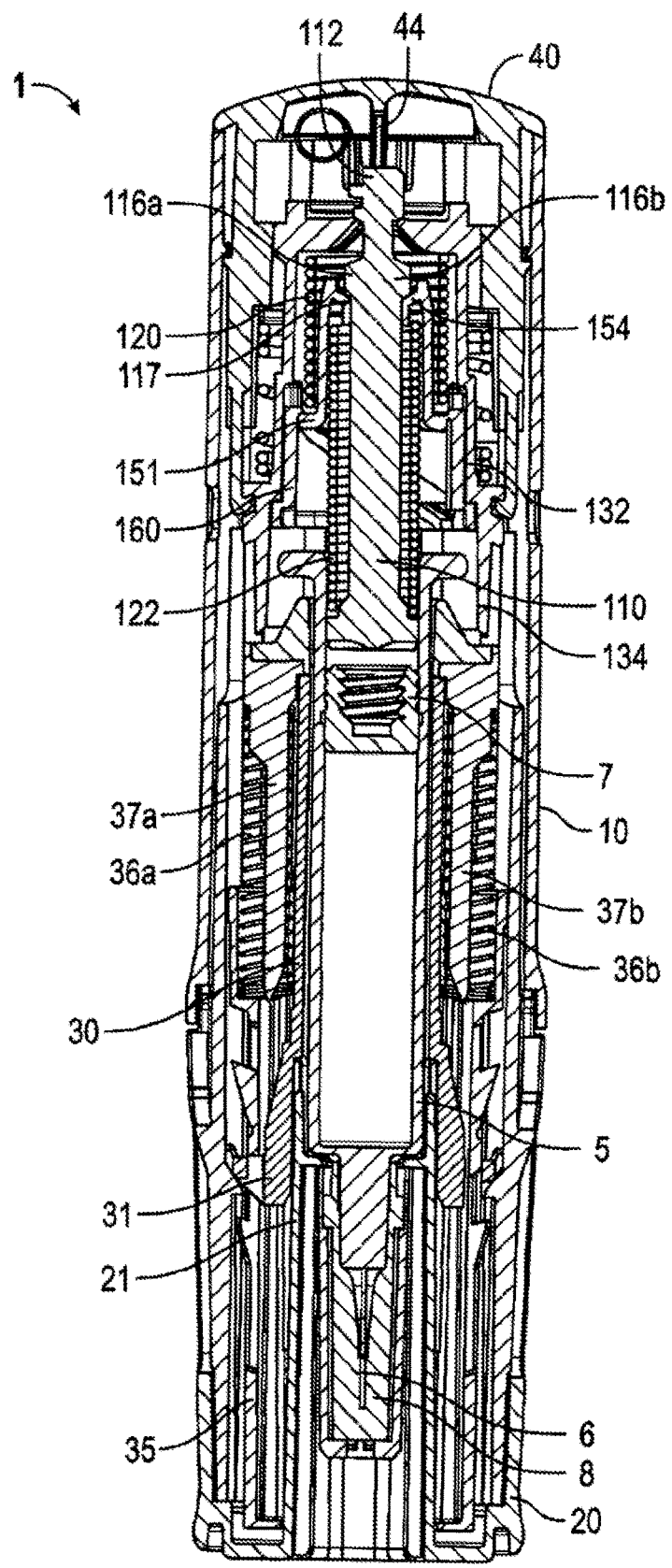
FIG. 1 is a cross-sectional view of a prior art injection device.

FIG. 1 shows a cross-sectional view of a prior art autoinjector 1 as disclosed in WO2016/189286. The autoinjector comprises a housing 10 within which is provided a syringe 5 of medicament. The housing 10 has a generally elongate tubular shape with a generally oval cross-sectional profile (and has a longitudinal axis running through the centre of the syringe).

The syringe 5 is a conventional syringe having a bung 7 within its body and a needle 6 at its forward end which may be initially protected (so as to remain sterile) by a removable needle shield or "boot" 8. The illustrated autoinjector 1 is generally intended to be a single use device (although the skilled person will appreciate that the invention is not limited to such devices) and, therefore, the view of FIG. 1 may typically represent a fully assembled, ready to use device as provided to an end user. A cap 20 is provided which closes the forward end of the autoinjector 1 prior to use. The cap 20 may include an internal formation, comprising rearward extending members 21, arranged to engage the removable needle shield 8 of the syringe 5 such that removal of the cap 20 from the housing 10 during use also removes the removable needle shield 8 from the syringe 5.

The autoinjector 1 may conveniently be considered to comprise a forward subassembly in a forward portion of the housing 10 and a rearward assembly in a rearward portion of the housing 10. The two housing portions may be snap fit together during assembly. The forward subassembly may comprise the components which surround and/or are initially forward of the syringe 5. The rearward subassembly may comprise those components which are initially rearward of the syringe 5.

A forward portion of the housing 10 may contain a syringe carrier 30 for movably mounting the syringe within the housing 10 to enable automatic needle penetration. It may be noted that prior to the removal of the cap 20, the rearward extending members 21 of the cap 20 underlie spring fingers 31 of the syringe carrier 30. This arrangement thus prevents inward movement of the spring fingers 31 prior to removal of the cap 20 and, therefore, blocks unlatching of the syringe carrier 30 and prevents movement relative to the housing 20.

A needle shroud (or lock out shroud) 35 is also provided and arranged to shroud the needle after use (when the syringe 5 and syringe carrier 30 are in a forward position) to prevent needle stick injuries. The shroud 35 may be activated by a pair of side-by-side shroud springs 36a, 36b carried on respective spring guides 37a, 37b. Operation of the shroud 30 and carrier 35 is not described here in any detail. However, it may be noted that the arrangement substantially corresponds to the arrangement described in WO2012/085580.

A rearward portion of the housing 10 includes a trigger button 40 which is inserted into the rearward portion of the housing 10 from the rearward end so as to substantially close the rearward end of the housing 10. The trigger button 40 has a cup-like profile with side walls which are arranged to fit within (and be substantially concentric with) the rearward housing 30 and an end wall which closes the rear end of the housing. The trigger button 40 includes a pair of forwardly extending resilient arms 41a and 41b which are arranged to provide an engagement between the trigger button 40 and the injector 1.

Figure 2:
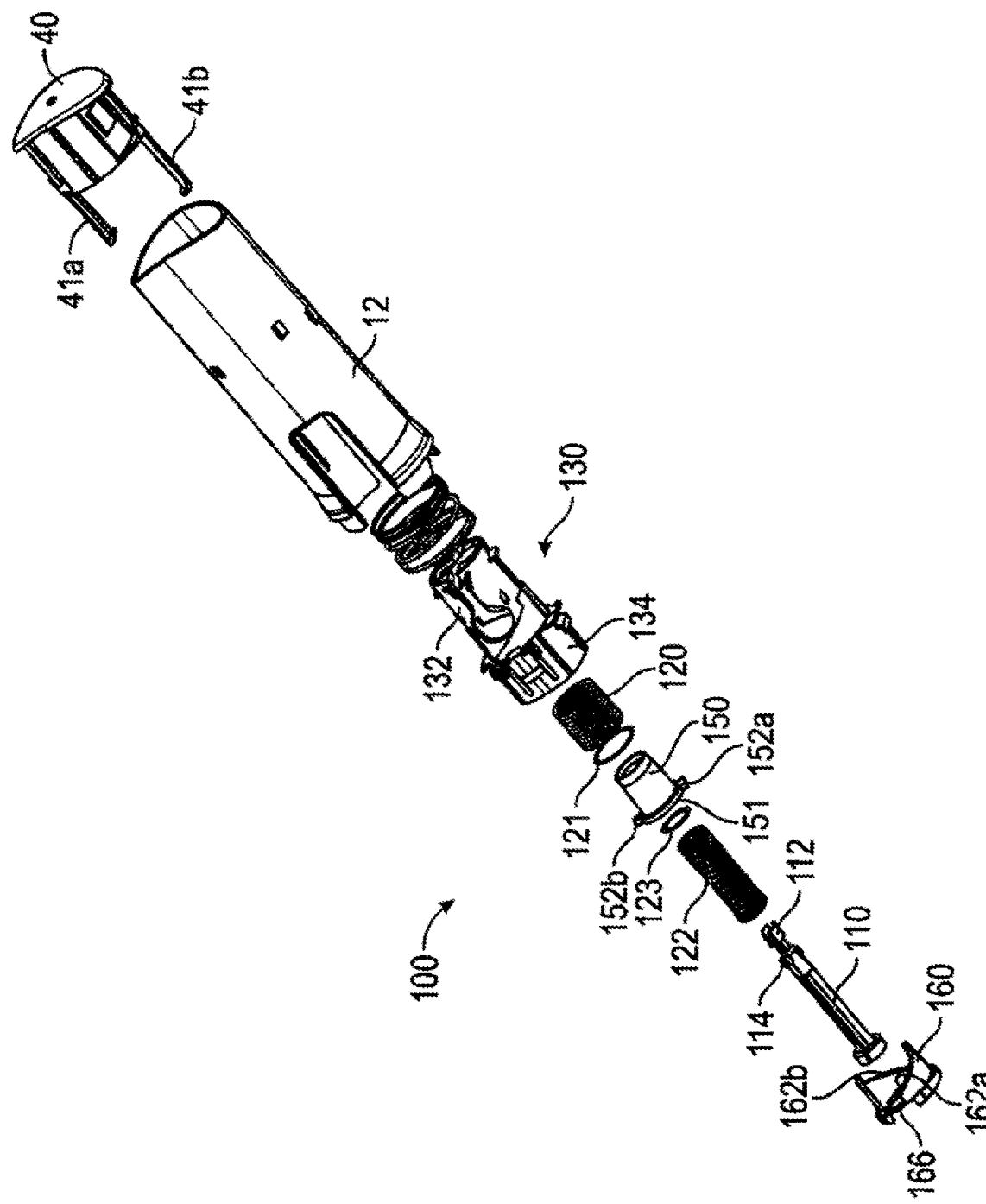
FIG. 2 is an exploded view of a rear section of a prior art injection device.

The rearward portion of the housing 10 also includes a drive mechanism 100, best seen in FIG. 2. The drive mechanism 100 includes a plunger 110 which is arranged to engage the bung 7 of the syringe 5 in use. The plunger 110 is driven forwards in use by a pair of concentric drive springs 120 and 122 (although it will be appreciated that in other embodiments a single spring may be used). An intermediate drive member in the form of a collar 150 (which also functions as part of the velocity regulator as described below) is provided between the first 120 and second 122 drive springs. A pair of thrust washers 121, 123 are provided respectively between the first 120 and second 122 springs and the drive member/collar 150. A latch 130 is arranged concentrically around the drive springs 120, 122, intermediate member/collar 150 and plunger 110. The latch 130 is arranged to hold the plunger 110 against the bias of the springs 120, 122 until the latch is released via the trigger button 40. The latch 130 comprises a rear body portion 132 having a split cylinder profile and defining a latch aperture at its rear end and a forward connecting body portion 134. The basic functional operation of the drive mechanism 100 is substantially as described, for example, in the applicants' earlier International Patent Applications WO2012/049484 and WO2015/011488.

Figure 3:
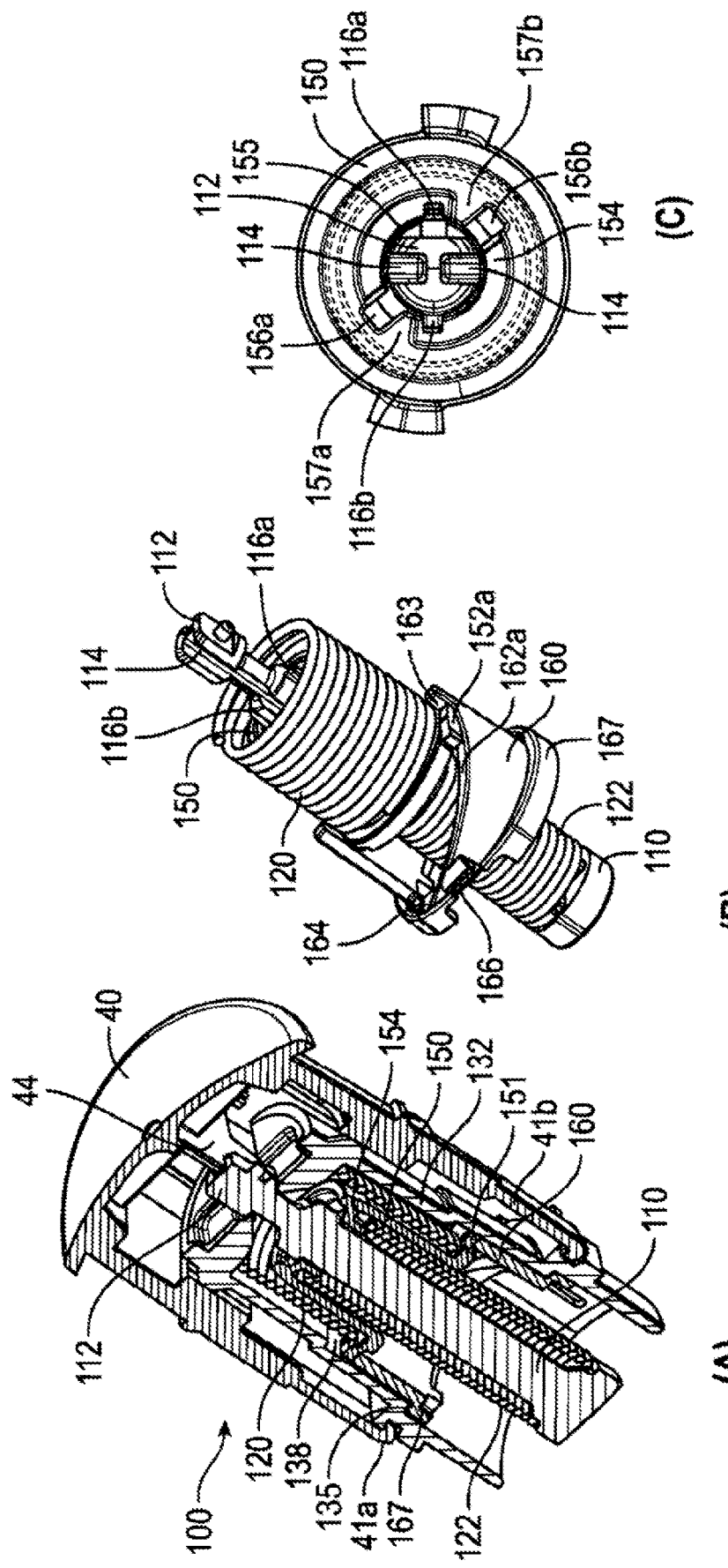
FIG. 3 is a cross-section view and partial end view of an actuation mechanism including a velocity regulator in accordance with an embodiment of the prior art, in a pre-fired state.
Figure 4:
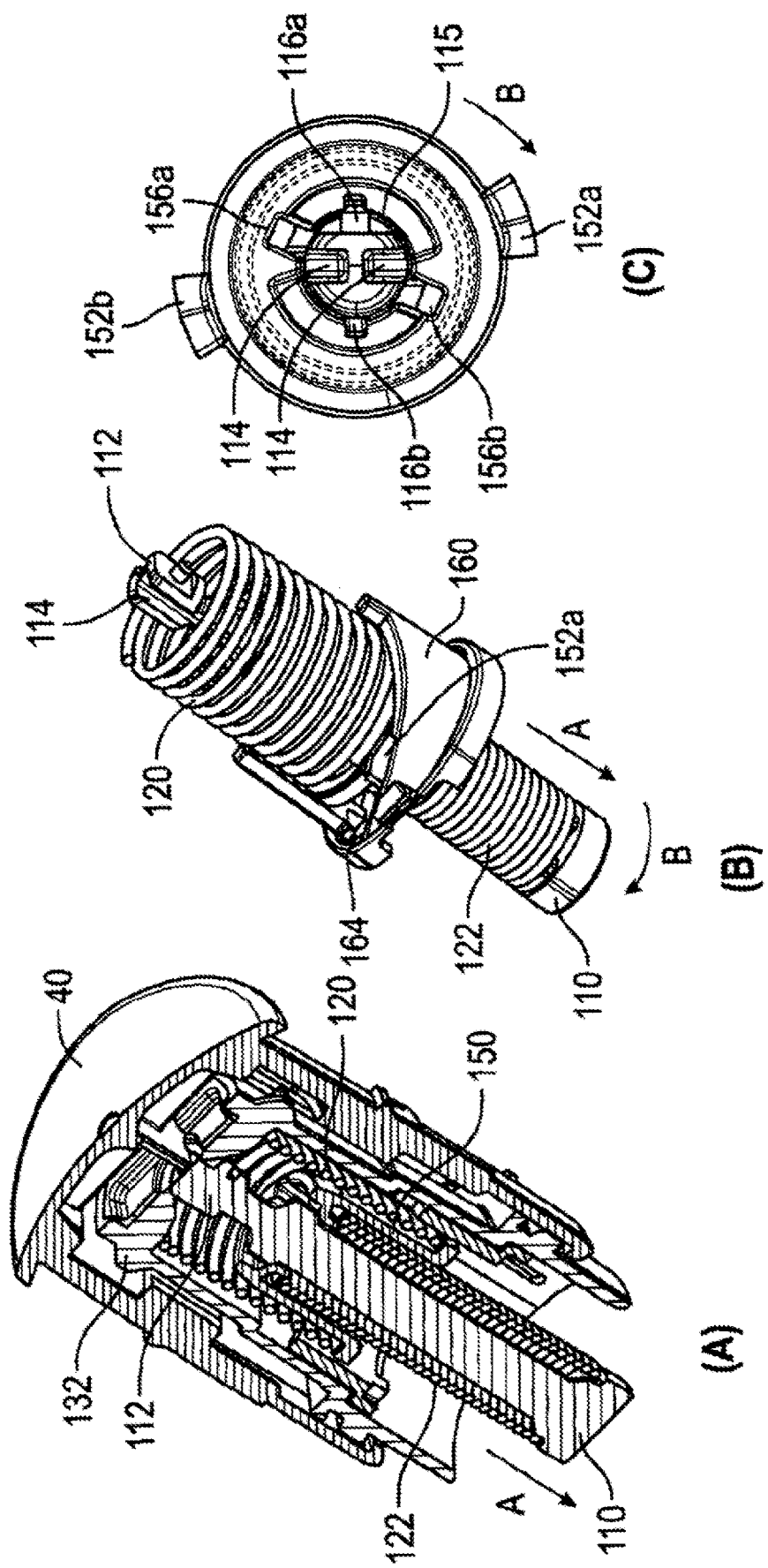
FIGS. 4 to 6 are sequential views corresponding to FIG. 3 during the activation of a prior art autoinjection device.

The driver mechanism will now be described in further detail with particular reference to FIGS. 2 and 3. FIG. 2 shows an exploded view of a rearward subassembly of the autoinjector device 1 (in which it may be noted that the housing 10 includes a discreet rearward housing component 12). In FIG. 3a the housing is omitted for clarity and in FIGS. 3b and 3c only the components directly associated with the velocity regulator are shown for further clarity. As noted above, the driver mechanism includes a latch member 130 which is removably fixed into the housing 10 (by a snap fit arrangement) and initially retains the plunger 110 against the forward biasing force of the actuation springs 120 and 122 (which act via the intermediate member 150). At the rear of the injection device 1 is provided a trigger button 40 which may initially be retained in position by the pair of arms 41a, 41b. In a central portion of the inner surface of the rearward face of the button 40 a forwardly extending boss 44 is provided which may act to urge the plunger 110 out of engagement with the latch member 130 during activation (in a manner such as that described in the applicants earlier patent applications referred to above).

The boss 44 comprises an arrangement which is in splined engagement with the rearward head 112 of the plunger 110. It will be seen that the rearward end of the plunger 110 is provided with a pair of axially extending radial slots which extend forwardly from the head 112 and the boss 44 comprising a corresponding pair of projections. As will be explained in further detail below, this arrangement ensures that the plunger 110 is rotationally fixed relative to the trigger button 40. In turn the trigger button 40 is non-rotationally engaged with the housing 10 (for example, due to the non-circular shape of the housing 10 and trigger button 40 and/or the engagement between the legs 41a, 41b of the trigger button 40 and the latch 130).

The driver mechanism 100 of the autoinjector device 1 also includes a velocity regulator arranged to control or limit the initial velocity of the plunger 110 upon release of the driver mechanism. The velocity regulator utilises a cam member 152 which travels along a cam surface 162 which provides an inclined plane along which the cam member 152 will travel during actuation.

The cam surface 162 is conveniently provided on a cam body 160 which is engaged with the forward portion 134 of the latch 130 by a snap-fit arrangement including, for example, at least one latch member 166. To ensure proper alignment between the cam body 160 and the latch member 130 an alignment flange 167 may also be provided on the cam body 160 to abut a corresponding shoulder 135 in the latch 130. The cam body 160 may comprise a generally annular body with an external profile which matches the required internal profile of the latch 130. A pair of helical cam surfaces 162a, 162b are defined at the rearward end of the cam body and are forwardly sloped to define a pair of parallel cam paths which extend circumferentially around the interior of the injection device 1 whilst also being inclined forwardly in the manner of a partial screw thread. A correspondingly profiled shoulder may be provided rearward of the cam surface 162 on the interior surface of the latch 130 such that when the cam body is assembled with the latch 130 a slot or track 138 as defined (and configured to receive the cam members 152). Each cam surface 162 is provided with stop 163 at its rearward end (which acts to separate the separate cam paths defined by the cam body 160) and ends with a cut-out or aperture 164 at the forward most end of the cam surface 162.

The collar 150 acts as an intermediate drive member between the first compression spring 120 and second compression spring 122. Accordingly, the collar 150 includes an external radial flange 151 at its forward end which provides a seat for the first compression spring 120 and an internal radial flange 154 at its rearward end which provides a seat for the second compression spring 122. The thrust washers 121, 123 are disposed on the seats between the radial flanges 151, 154 of the collar and the springs 120, 122. The collar 150 is a generally cylindrical body and is provided with a pair of radially opposed outwardly extending lugs 152a, 152b. The lugs 152a, 152b are provided on a radially outer surface of the outwardly extending flange 151 (such that they do not impede either of the compression springs 120, 122). The internal flange 154 at the rear of the collar 150 includes an aperture 155 through which the head 112 of the plunger extends when the driver mechanism 100 is in the pre-fired (or primed) condition as shown in FIG. 3.

The aperture 155 is provided with a keyed profile defined by a cylindrical central aperture portion 155a and a pair of opposed radial slots 156. The cylindrical side walls of the collar 150 extend rearward slightly beyond the flange 154 so as to define a cylindrical cup which surrounds the flange 154 and the aperture 155. Inwardly radially extending stop members 157a, 157b may be provided adjacent to one side of the radial slots 156a and 156b.

A rearward portion of the plunger 110 which is axially rearward of the aperture 155 in the pre-fired configuration is provided with a profiled cross-section for engagement with the keyway defined by the aperture 155. This profiled portion is immediately forward of the head 112 of the plunger which is configured to be engaged by the latch 130. The profiled portion is defined by a pair of radially outwardly 20 extending projections 116a, 116b which provide a forward facing shoulder 117 is initially engaged with the rearward face of the flange 154. The radial projections 116a, 116*b* are configured such that they may pass through the radial slots 156*a*, 156*b* when the slots 156 and projections 116 are aligned.

The actuation sequence of the mechanism 100 and velocity regulator will now be described with reference to FIGS. 3 to 6. The pre-firing configuration of the driver mechanism 100 is shown in FIG. 3. In this configuration the head 112 of the plunger 110 is retained in the aperture of the latch 130. As such both the first compression spring 120 and the second compression spring 122 are in a compressed, energised, state. The trigger button 40 is in splined engagement with the rearward end of the plunger 110 via the boss 44 being positioned within the slots 114 at the rear of the plunger 110. The rearward portion 132 of the latch 130 is unable to expand to release the head 112 of the plunger 110 as part of the trigger button abuts an outer surface of the rearward section of the latch 132.

In this position the radial projections 116 of the plunger 110 are rearwardly positioned relative to the aperture 155 of the collar 150 and the relative rotational position of the plunger 110 and the collar 150 has been set during assembly such that the projections 116 are misaligned with the slots 156 and, in fact, it will be noted that the projections 116 may be abutting against the stops 157 of the collar 150. In this initial position the cam members 152 are positioned at a rearward end of the cam surfaces 162 and essentially abut against the stops 163 at the rearward most end of the cam surfaces 162.

In order to activate the device the user urges the trigger button 40 forward relative to the housing 10 of the autoinjector device 1 (having firstly carried out any required initiation steps such as removal of the cap from the forward end of the autoinjector device 1 and/or releasing any safety mechanisms, such as an interlock). The forward movement of the trigger button 40 moves the blocking arrangement of the cap 40 out of alignment with the rearward section 132 of the latch 130 and may also directly transmit a forward force onto the rear of the plunger 110 via the engagement of the boss 44 with the head 112 of the plunger 110. As the result of this trigger action, the head 112 of the plunger 110 is released from the trigger 130 freeing the rearward spring 120 to urge the plunger forwardly, in the direction of arrow A, via the outer flange 151 or the collar 150.

This forward movement causes the cam members 152*a*, 152*b* to travel along the inclined path of the cam surface 162*a*, 162*b*. As the first spring 120 expands its axial force is transmitted by the collar 150 through the fully compressed second compression spring 122 to the forward end of the plunger 110. However, initially the plunger 110 is unable to travel beyond the collar 150 as the radial projections 116 engage the internal flange 154 at the rear of the collar 150.

Due to the splined engagement between the trigger button 40 and the plunger 110 the collar 150 must rotate relative to the plunger 110, in the direction of the arrow B, as the cam members 152*a*, 152*b* travel along the cam surfaces 162*a*, 162*b*. The thrust washers 121, 122 prevent or reduce any frictional resistance to the rotation of the collar 150 by the springs 121, 122. As best seen in the end view of FIG. 4*c*, the resulting relative rotation of the collar 150 causes the aperture 155 to rotate relative to the radial projections 116*a*, 116*b* moving the projections off the stop surface 157 and towards the radial slots 156*a*, 156*b*.

In other arrangements, and as would be clear to a skilled person, the trigger may comprise and actuator that moves rearwards on application of the auto-injector 1 to an injection site. In some arrangements, the actuator may comprise a forward portion of the auto-injector and pressing the forward end against the injection site may produce a force to move the actuator rearwards. The movement of the actuator rearwards may release the trigger mechanism by any known means.

Figure 5:
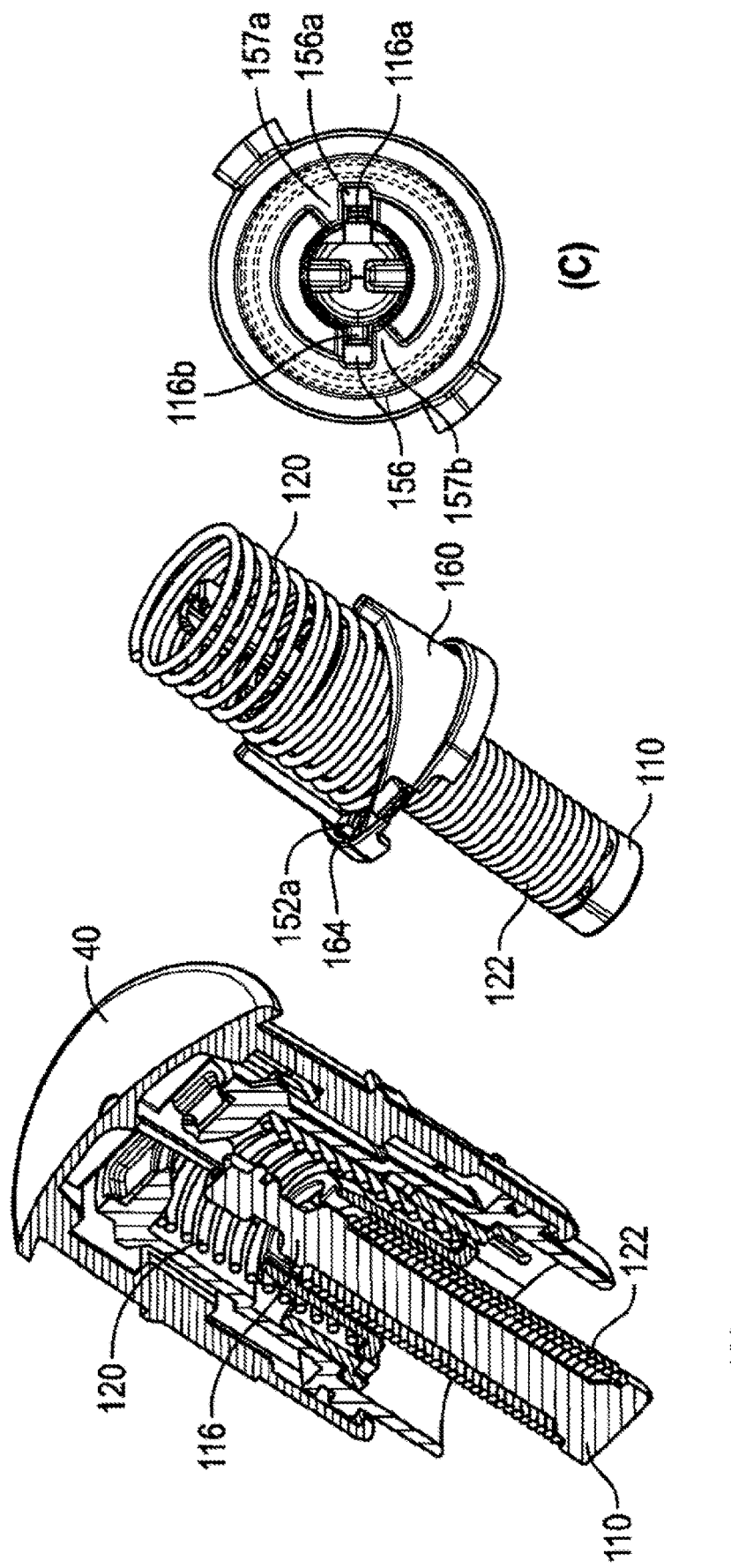

As the plunger 110 and collar 150 continue to move forwardly, the collar 150 reaches its fully rotated position as shown in FIG. 5. In the illustrated example the fully rotated position corresponds to approximately one half turn of the collar 150 (although the skilled person will appreciate that the particular configuration may vary depending on the profile of the cam surface and the required sequencing of the actuation mechanism 100). In this position the radial slots 156*a*, 156*b* have rotated into alignment with the radial projections 116*a*, 116*b* and the cam members 152*a*, 152*b* have also reached the end of the cam surface 162*a*, 162*b* and have moved into alignment with the cut-out/aperture 164 at the end of the cam path.

Figure 6:
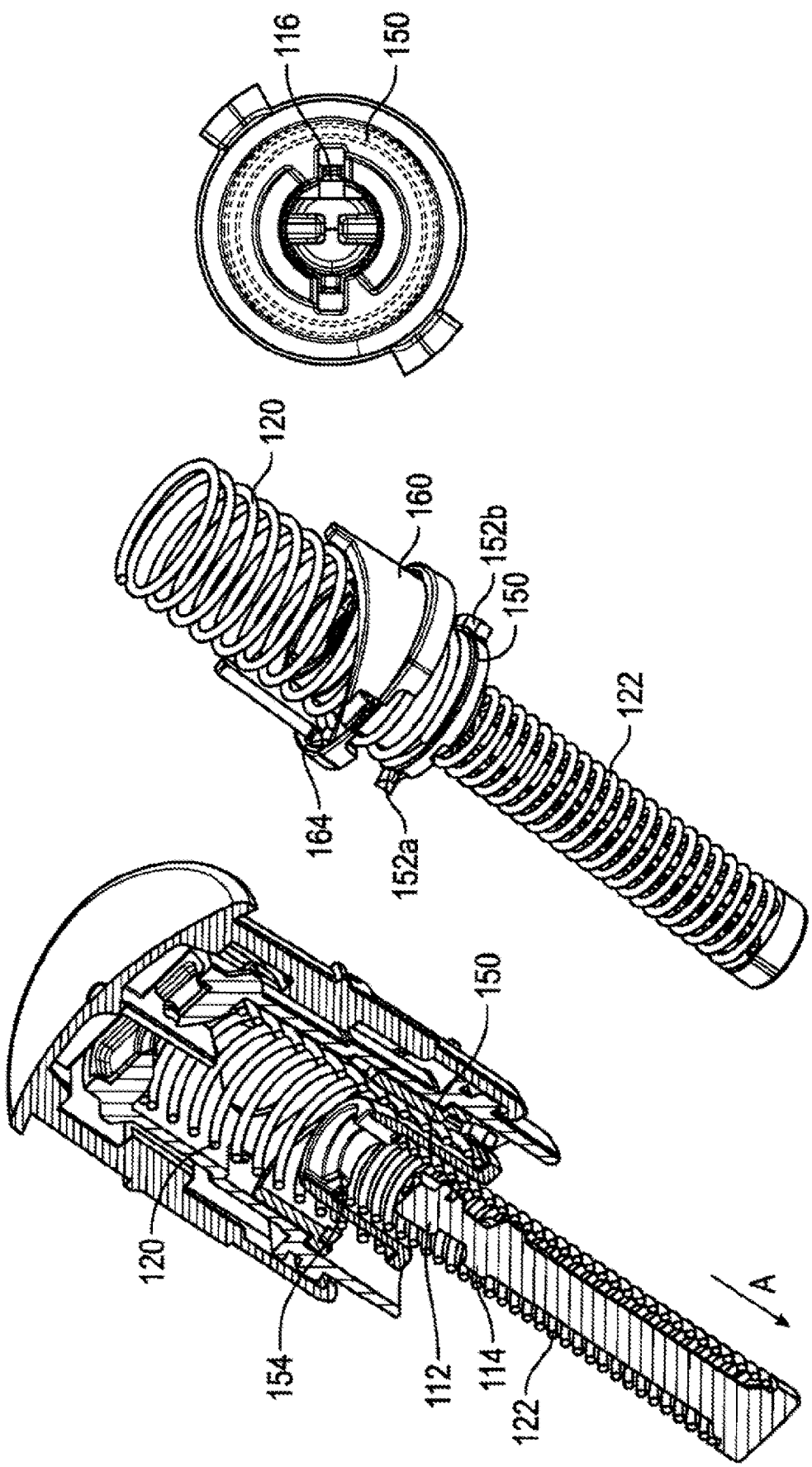

Accordingly, as shown in FIG. 6, the velocity regulator may now disengage so as to allow the plunger to continue freely forward (continuing in the direction of arrow A). In this forward movement the plunger 110 moves forward relative to the collar 150 due to the radial projections 116*a*, 116*b* passing through the radial slots 156*a*, 156*b* and the collar 150 is also allowed to pass forwardly of the cam body 160 due to the cam members 152*a*, 152*b* passing through the cut-outs 164. In other words, both the collar 150 and plunger 110 are disengaged and the collar 150 and cam body 160 are disengaged. In the illustrated embodiment the disengagements both occur substantially simultaneously (although the skilled person will appreciate that this may depend on the particular sequencing required). Once the velocity regulator is disengaged the forward motion of the plunger 110 is no longer regulated (but the skilled person will appreciate that the plunger may now be pressing against the medicament within the syringe 5 such that its motion is naturally damped).

Although the device has been described above with reference to one embodiment, it will be appreciated that various changes or modifications may be made. For example, the skilled person will appreciate that the timing of the disengagement between the components of the velocity regulator may depend on the particular configuration of the device. For example, the velocity regulator may be intended to slow/control the movement of the plunger 110 only during an initial movement in which the plunger 110 is brought into contact with the bung 7 of the syringe 5 (since manufacturing tolerances will usually make it necessary for the forward end of the plunger 110 to be initially spaced from the rearward end of the bung 7) so as to reduce impact thereto. Alternatively, or additionally, the velocity regulator may be configured to control the speed of movement of the actuation mechanism until the needle insertion step of the actuation process has been completed. Whilst the illustrated example includes two opposing counter-surfaces the skilled person will appreciate that more or less features may be utilised in embodiments of the invention.

In the illustrated device the cam surface defines a substantially constant helical cam path but the skilled person will appreciate that the surface may have other sloped profiles (for example, a variable angle of incline) depending upon the velocity profile required for the forward movement of the plunger 110. Whilst an arrangement having two compression springs is advantageous in providing a compact actuation mechanism the skilled person will appreciate that in some embodiments only a single compression may be utilised. For example, in a single spring arrangement, the cam members could be formed on a portion of the plunger and the plunger may be allowed to rotate relative to the housing.

Generally disclosed herein are exemplary injection devices that may comprise components of the prior art device described above. The exemplary injection device may comprise modifications to the components of the prior art device described above, or additional components.

The inventors have realised that the force required to release a force applied by a driver mechanism when in a primed state using a trigger mechanism in known injection devices (such as described above) is increased when the force applied is relatively high. That is, a force required to activate the trigger mechanism, which is typically applied by a user's thumb, may be high when a high force driver mechanism, which may comprise a spring such as the springs 120, 122 disclosed above is used. Such high force driver mechanisms may be used for delivery of a high viscosity medicament, for example.

In the exemplary injection device 100 of FIG. 1, the greater the force of the rearward spring 120, the greater the force exerted against the latch member 130 which retains the rearward spring 120 in compression. In turn, the frictional force between the latch member 130 and the rearward spring 120 that the user is required to overcome when pressing the trigger button 40 to actuate the device is also increased.

Generally disclosed herein is an alternative rearward arrangement of an injection device which allows for a low actuation force even when a high force driver mechanism, such as a spring, is utilised. The arrangement further allows gradual release of the driver mechanism.

Exemplary injection devices are configured such that a driver mechanism, which may comprise a spring as in the injection device 1 described above, is retained in a primed state by engagement with a ramped surface of a trigger mechanism. In exemplary injection devices the ramped surface is withdrawn from engagement with the driver mechanism on actuation of the trigger mechanism. For example, the trigger mechanism may comprise a trigger button and may be actuated by a user applying a force thereto. Withdrawal of the ramped surface from engagement with the driver mechanism releases the driver mechanism from the primed state. In exemplary injection devices, upon release of the driver mechanism from its primed state, a syringe may be driven forwards for insertion of a needle of the syringe into an injection site. Alternatively or in addition, a bung of the syringe may be driven forwards for delivery of a dose of medicament.

The term "primed state" encompasses a driver mechanism that is positioned such that it is capable of applying a biasing force to one or more features of the injection device. In the case of a driver mechanism comprising a biasing means, such as a spring, they may be at least partly tensioned when in a primed state such that a force is applied to return to the spring to its resting state.

Figure 7A:
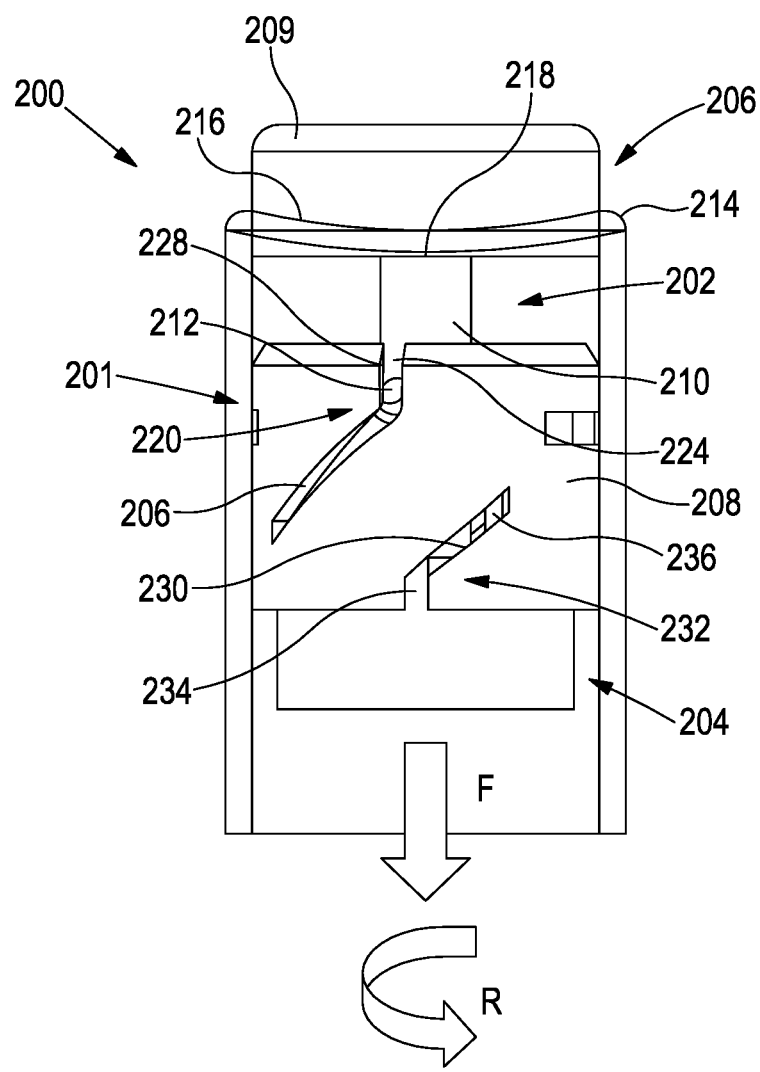
FIGS. 7a-c show an injection device at various stages of operation.

FIG. 7a shows a rearward portion of an injection device 200. The rearward portion of the injection device 200 houses a release mechanism 201 comprising a trigger mechanism 202 and a driver mechanism 204.

In the exemplary embodiment of FIG. 7a, the trigger mechanism 202 comprises a trigger 206 and a collar 208.

In the exemplary injection device 200, the trigger 206 comprises a trigger button 209, a shaft 210 and a trigger lug 212. The trigger 206 is configured to be slidably received within a housing 214. The housing 214 may be the housing of an injection device 200 within which the release mechanism 201 is configured to operate. In the exemplary embodiment of FIG. 7a, the cross section of the trigger button 209 of the trigger 206 is substantially the same as the cross section of an opening 216 of the housing 214.

FIG. 7a shows the injection device 200 in a first position, prior to use, in which the trigger button 209 of the trigger 206 protrudes from the opening 216 of the housing 214. The trigger button 209 is configured to receive the thumb/fingers of a user such that the user may apply a force to the trigger button 209 to move the trigger 206 within the housing 214.

The trigger 206 may be configured to move linearly within the housing 214. The trigger 206 may be prevented from rotating within the housing 214 of the injection device 200 such that only linear movement of the trigger 206 is possible. For example, as described above, the trigger 206 may comprise a boss in splined engagement with another component of the injection device 200.

After use, the trigger button 209 of the trigger 206 is located substantially within the opening 216 of the housing 214 such that it does not protrude from the opening 216, or such that the protrusion is reduced relative to the prior to use state.

The shaft 210 extends forwards from the trigger button 209. In the exemplary injection device 200, the shaft 210 extends from the centre of the trigger button 209. In alternative embodiments the shaft 210 may extend from a position on the trigger button 209 which is offset from the centre of the trigger button 209. The shaft 210 is cylindrical however alternative cross sectional shapes may be used.

The trigger lug 212 is positioned on the shaft 210 at a predefined distance from a lower surface 218 of the trigger button 209. The trigger lug 212 is configured to engage with the collar 208 of the release mechanism 201. The collar 208 may be configured to be rotatable within the housing 214 but fixed axially such that the collar 208 does not move linearly within the housing 214. The trigger lug 212 may engage with the collar 208 to cause rotation of the collar 208 within the housing 214 on linear displacement of the trigger button 209. In the exemplary collar 208 of the injection device 200, the trigger lug 212 is configured to engage with a trigger track 220 on the collar 208. The trigger track 220 is configured to receive the trigger lug 212 and allow travel of the trigger lug 212 within the trigger track 220.

The trigger track 220 comprises an axial (or vertical) section 224 and a ramped section 226. The axial section 224 extends longitudinally (with respect to the injection device) from a rearward surface of the collar 208. The axial section 224 is configured to receive the trigger lug 212 prior to actuation of the trigger mechanism 202, when the trigger 206 is in the first position, as shown in FIG. 7a. The axial section 224 comprises a locking surface 228 which may be biased against the trigger lug 212 as a result of the engagement between the collar 208 and the driver mechanism 204, as explained below. The interaction between the axial section 224 and the trigger lug 212 prevents rotation of the collar 208.

The ramped section 226 of the trigger track 220 is angled with respect to the axial section 224 and extends from a forward end thereof. The ramped section 226 may be configured to engage with the trigger lug 212 to gradually release the driver mechanism 204 from the primed state. The ramped section 226 may interact with the trigger lug 212 when the user applies a force to the trigger button 209 causing the trigger lug 212 to travel within the ramped section 226. In exemplary embodiments the ramped section 226 may be helical in that it extends around an outer wall of the broadly tubular collar. In the exemplary embodiment of FIG. 7a, the trigger track 220 is configured such that the trigger lug 212 enters the ramped section 226 once disengaged from the axial section 224.

The collar 208 may further comprise a ramped surface 230. In the exemplary injection device 200 the collar 208 comprises a release track 232 and the ramped surface 230 forms part of the release track 232. The release track 232 may further comprise an axial release section 234. In the exemplary injection device 200, the ramped surface 230 of the release track 232 may be of the same orientation as the ramped section 226 of the trigger track 220. That is, the ramped surface 230 may extend broadly in the same direction as the ramped section 226. In exemplary arrangements, the ramped surface 230 may be substantially parallel to the ramped section 226, although in other arrangements the ramped surface 230 may be at a different angle to the ramped section 226. Having the ramped surface 230 at a different angle to the ramped section 226 allows the rate of release of the driver mechanism 204 to be geared. For example, if the ramped surface 230 is inclined at a greater angle to the vertical than the ramped section 226, a quicker release of the driver mechanism 204 will be achieved. The ramped surface 230 may be configured to engage with the driver mechanism 204 and to retain it in a primed state.

The driver mechanism 204 may comprise a release lug 236. The release lug 236 may be configured to engage with the ramped surface 230. In the exemplary arrangement of FIG. 7a, the release lug 236 is received within the release track 232 to engage with the ramped surface 230. The release track 232 may be configured to allow the release lug 236 to travel within the release track 232.

The driver mechanism 204 may be configured to exert a force to bias the release lug 236 onto the ramped surface 230. In exemplary arrangements, the driver mechanism 204 may comprise a compression spring (not shown) configured to exert a biasing force on the release lug 236. Alternatively, the driver mechanism may comprise any other driving means that acts to bias the release lug 236 onto the ramped surface 230.

The driver mechanism 204 may be slidably fitted within the housing 214. The driver mechanism may be prevented from rotating within the housing 214, such that only linear movement of the driver mechanism 204 is possible.

Figure 7B:
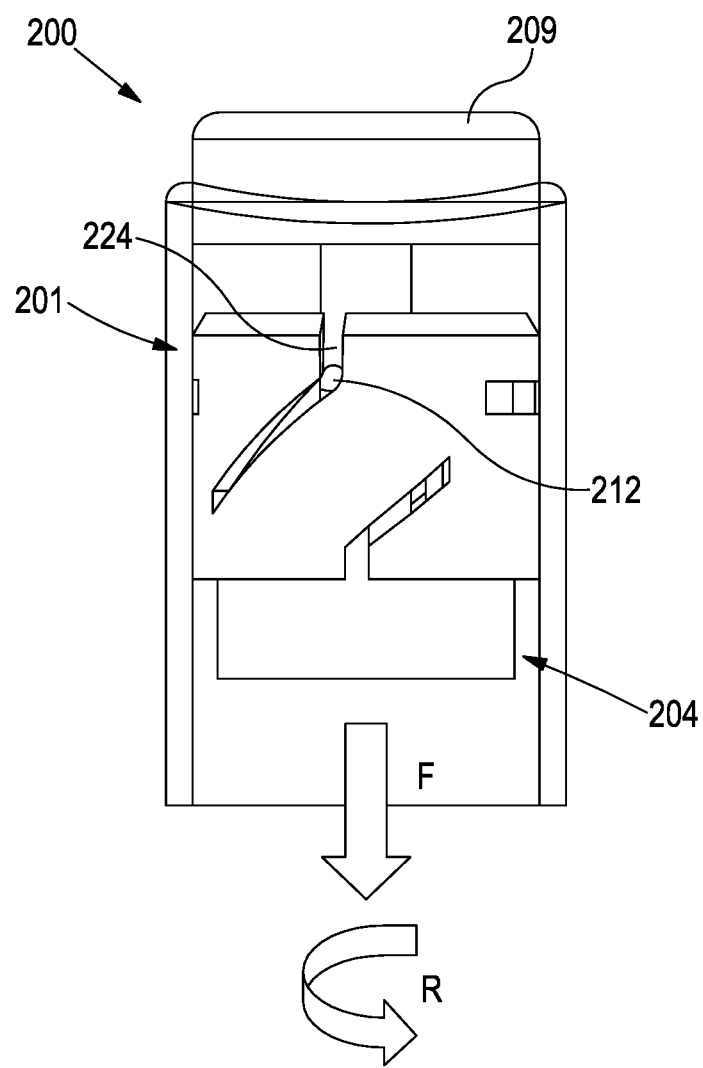
Figure 7C:
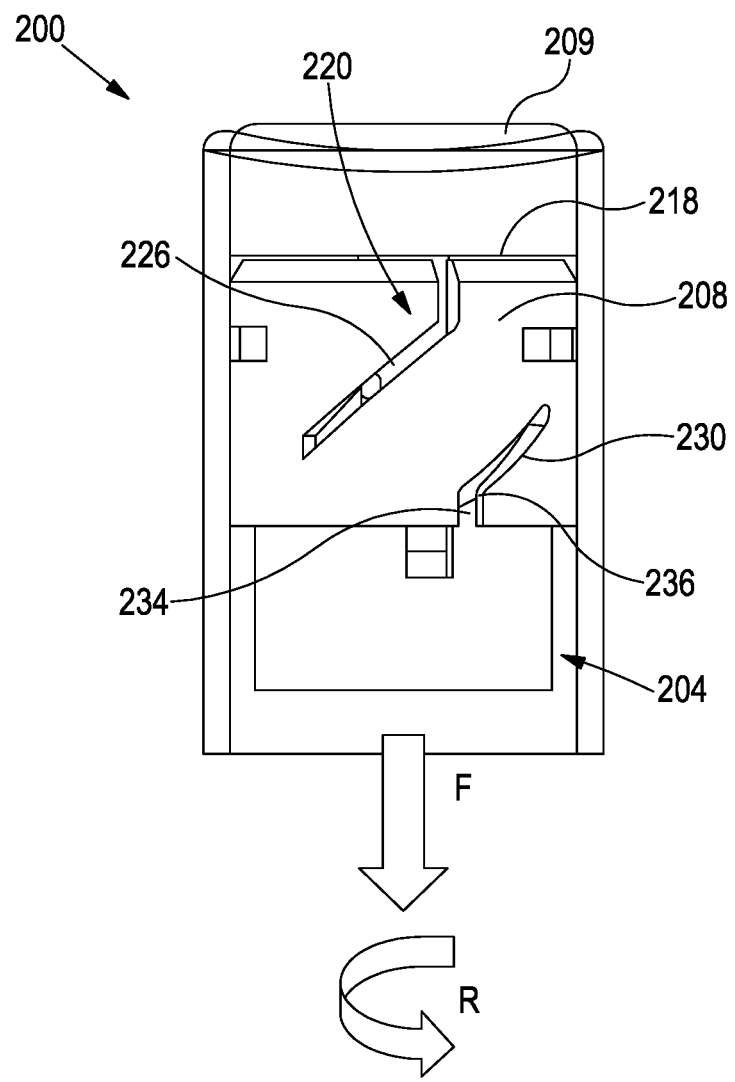

FIGS. 7a-c show the injection device 200 at various positions prior to and after actuation of the trigger mechanism 202. The operation of the injection device 200 will be described below with reference to FIGS. 7a-c.

FIG. 7a shows the injection device 200 prior to actuation of the trigger mechanism 202. The trigger button 209 of the trigger 206 protrudes from the housing 214 of the injection device 200 and the lower surface 218 of the trigger button 209 is separated from the collar 208 to provide clearance for forward displacement of the trigger button 209. The trigger lug 212 is located in the axial section 224 of the trigger track 220. When the trigger lug 212 is located within the axial section 224 of the trigger track 220, rotation of the collar 208 is prevented as described below.

The driver mechanism 204 may comprise a compression spring (not shown) which applies a forward biasing force to the release lug 236. This may be in the direction F as shown in FIG. 7a. The forward force acts to urge the release lug 236 forwards along the ramped surface 230, which in turn urges the collar 208 to rotate in the direction R. The rotation of the collar 208 is resisted by the interaction between the trigger lug 212 and the locking surface 228 of the axial section 224 of the trigger track 220. As such, when the trigger lug 212 is engaged with the axial section 224, the collar 208 is unable to rotate under the forward force and the ramped surface 230 is therefore prevented from being withdrawn from engagement with the driver mechanism 204, which is retained in the primed state.

A user applies a force to the trigger button 209. The force applied to the trigger button 209 moves the trigger 206 within the housing 214 towards the forward end of the injection device 200. As a result, the trigger lug 212 travels within the axial section 224 of the trigger track 220 on the collar 208.

FIG. 7b shows the release mechanism 201 of the injection device 200 in an unlocked state. The trigger button 209 has traveled forward such that the trigger lug 212 exits a forward end of the axial section 224. The collar 208 is no longer prevented from rotating under the force of the driver mechanism 204.

The user continues to displace the trigger button 209 forwards such that the trigger lug 212 travels within the ramped section 226 of the trigger track 220 as shown in FIG. 7c. This rotates the collar 208 in the direction R. The rotation of the collar 208 causes withdrawal of the ramped surface 230 from engagement with the release lug 236 of the driver mechanism 204. Withdrawal of the ramped surface 230 causes the release lug 236 to travel forwards along the ramped surface 230. The driver mechanism 204 is therefore released from the primed state gradually along the ramped surface 230 and is free to drive either insertion of the needle or delivery of the medicament after the release lug 236 reaches the end of the ramped surface 230 and enters the axial release section 234.

The amount of force required to initially actuate the trigger mechanism 202 is only required to overcome the friction between the trigger lug 212 and the axial section 224 of the trigger track 220 on the collar 208 and is therefore much smaller than the driving force exerted by the driver mechanism 204. The driver mechanism 204 exerts a linear force F on the collar 208, which is translated into a rotational force R by the ramped surface 230 of the release track 232. The amount of rotational force R is a fraction of the amount of linear force F exerted by the driver mechanism 204. The fraction is determined by the gradient of the ramped surface 230. Therefore, when the trigger lug 212 is in the axial section 224 of the trigger track 220, the force R is acting laterally on the trigger lug 212 via the locking surface 228 and is less than the linear force F imparted by the driver mechanism 204. The friction force between the locking surface 228 and the trigger lug 212 is, in one exemplary arrangement, about 10% to 20% (which may be affected by materials) of the rotating force R. Movement of the trigger lug 212 from the axial section 224 into the ramped section 226 of the trigger track 220 for actuating the trigger mechanism therefore requires a reduced force.

As described above, the driver mechanism 204 exerts a force on the release lug 236 in a forward direction (the direction of arrow F). Because the ramped surface 230 of the driver mechanism 204 is inclined, the forward force F exerted on the release lug 236 by the driver mechanism 204 acts to rotate the collar 208 in the direction R indicated. The rotation of the collar 208 under the force of the driver mechanism 204 aids the release of the driver mechanism 204 and therefore reduces the force required. Because the ramped surface 230 of the collar 208 is inclined with respect to the vertical, the release of the driver mechanism from the primed state is gradual.

The collar 208 rotates under the force of the driver mechanism 204 until the ramped surface 230 is withdrawn from engagement with the driver mechanism 204.

The invention claimed is:

1. An injection device for receiving a syringe therein and for delivering a dose of medicament from the syringe, the injection device comprising:
   a driver mechanism comprising a biasing member and being retainable in a primed state and releasable from the primed state for driving one or more features of the injection device forward,
   a trigger mechanism comprising a rotatable collar and a ramped surface, the ramped surface engaged with the driver mechanism to retain the driver mechanism in the primed state,
   wherein the driver mechanism further comprises a release lug configured to engage the ramped surface and wherein the trigger mechanism is configured on actuation thereof to withdraw the ramped surface from engagement with the driver mechanism for release thereof.

2. The injection device according to claim 1, wherein the rotatable collar comprises the ramped surface, and wherein actuation of the trigger mechanism comprises rotation of the collar.

3. The injection device according to claim 2, wherein the trigger mechanism is configured to translate a linear actuation force into rotation of the collar.

4. The injection device according to claim 3, wherein the trigger mechanism comprises a trigger lug configured to engage with a ramped section of a trigger track on the collar for rotating the collar.

5. The injection device according to claim 4, wherein the trigger track further comprises an axial section, and wherein the trigger lug is configured to engage with the axial section, such that rotation of the collar is prevented when the driver mechanism is retained in the primed state.

6. The injection device according to claim 1, further comprising a trigger configured to be operated by a user and to actuate the trigger mechanism when operated.

7. The injection device according to claim 6, wherein the trigger comprises an actuator configured to move rearward under a force resulting from pressing a forward end of the injection device against an injection site.

8. The injection device according to claim 7, wherein the rotatable collar comprises the ramped surface, and wherein actuation of the trigger mechanism comprises rotation of the collar;
   wherein the trigger mechanism comprises a trigger lug configured to engage with a ramped section of a trigger track on the collar for rotating the collar; and
   wherein the trigger mechanism is configured to translate a linear actuation force into rotation of the collar,
   wherein the trigger lug is directly coupled to the trigger button or the actuator, and wherein operation of the trigger button or the actuator causes the trigger lug to engage with the ramped section of the trigger track.

9. The injection device according to claim 6 wherein the trigger comprises a trigger button configured to be operated by depression thereof by the user.

10. The injection device according to claim 1, wherein the driver mechanism exerts a force biasing the release lug onto the ramped surface for assisting the withdrawal of the ramped surface.

11. The injection device according to claim 1, wherein the biasing member comprises a compression spring.

12. The injection device according to claim 1, wherein the driver mechanism is configured to drive forward one or more of: the syringe for insertion of a needle of the syringe into an injection site; and a plunger of the syringe for delivery of the dose of medicament.

13. A trigger mechanism for use in an injection device for receiving a syringe therein and for delivering a dose of medicament from the syringe, the trigger mechanism comprising:
   a ramped surface configured to engage with a driver mechanism comprising a release lug configured to engage the ramped surface, the ramped surface configured to retain the driver mechanism in a primed state,
   the trigger mechanism being configured such that, on actuation thereof, the ramped surface is withdrawn from engagement with the driver mechanism for release of the driver mechanism.

14. The trigger mechanism according to claim 13, further comprising a rotatable collar, which comprises the ramped surface, and wherein actuation of the trigger mechanism comprises rotation of the collar.

15. The trigger mechanism according to claim 14 configured to translate a linear actuation force into rotation of the collar.

16. The trigger mechanism according to claim 15 comprising a trigger lug configured to engage with a ramped section of a trigger track on the collar for rotating the collar.

17. The trigger mechanism according to claim 16, wherein the trigger track further comprises an axial section, and wherein the trigger lug is configured to engage with the axial section, such that rotation of the collar is prevented when the driver mechanism is retained in the primed state.

18. The trigger mechanism according to claim 13, further comprising a trigger configured to be operated by a user and to actuate the trigger mechanism when operated.

19. The injection device according to claim 18, wherein the trigger comprises an actuator configured to move rearward under a force resulting from pressing a forward end of the injection device against an injection site.

20. The trigger mechanism according to claim 19, further comprising a rotatable collar, which comprises the ramped surface, and wherein actuation of the trigger mechanism comprises rotation of the collar,
   wherein the trigger mechanism is configured to translate a linear actuation force into rotation of the collar,
   comprising a trigger lug configured to engage with a ramped section of the trigger track on the collar for rotating the collar, wherein the trigger lug is directly coupled to the trigger button or the actuator, and wherein operation of the trigger button or the actuator causes the trigger lug to engage with the ramped section of the trigger track.

21. The trigger mechanism according to claim 18 wherein the trigger comprises a trigger button configured to be operated by depression thereof by the user.

* * * * *